US010966656B2

(12) United States Patent
Nagai et al.

(10) Patent No.: US 10,966,656 B2
(45) Date of Patent: Apr. 6, 2021

(54) ELECTRIC CONDUCTIVE FIBER STRUCTURE, ELECTRODE MEMBER, AND METHOD OF PRODUCING ELECTRIC CONDUCTIVE FIBER STRUCTURE

(71) Applicants: Toray Industries, Inc., Tokyo (JP);
Nagase ChemteX Corporation, Osaka (JP)

(72) Inventors: Noriko Nagai, Shiga (JP); Keiji Takeda, Shiga (JP); Jun Kawakami, Shiga (JP); Hiroshi Nagata, Hyogo (JP); Tatsuya Ohori, Hyogo (JP)

(73) Assignees: Toray Industries, Inc., Tokyo (JP);
Nagase ChemteX Corporation, Osaka (JP)

(*) Notice: Subject to any disclaimer, the term of this patent is extended or adjusted under 35 U.S.C. 154(b) by 237 days.

(21) Appl. No.: 16/094,220

(22) PCT Filed: Mar. 30, 2017

(86) PCT No.: PCT/JP2017/014300
§ 371 (c)(1),
(2) Date: Oct. 17, 2018

(87) PCT Pub. No.: WO2017/183463
PCT Pub. Date: Oct. 26, 2017

(65) Prior Publication Data
US 2019/0090810 A1 Mar. 28, 2019

(30) Foreign Application Priority Data
Apr. 18, 2016 (JP) .............................. JP2016-083183

(51) Int. Cl.
*H01B 1/24* (2006.01)
*A61B 5/00* (2006.01)
(Continued)

(52) U.S. Cl.
CPC .............. *A61B 5/6804* (2013.01); *A61B 5/25* (2021.01); *A61B 5/291* (2021.01); *C08L 25/06* (2013.01);
(Continued)

(58) Field of Classification Search
CPC ... A61B 5/6804; A61B 5/0408; A61B 5/0478; A61B 5/0492; A61B 2562/0209;
(Continued)

(56) References Cited

U.S. PATENT DOCUMENTS 4,975,317 A * 12/1990 Kuhn ..................... D06M 11/28
427/389.9
5,211,810 A * 5/1993 Bartholomew ...... C08G 61/122
162/127

(Continued)

FOREIGN PATENT DOCUMENTS

CA 2 127 919 3/1995
CN 1860261 A 11/2006
(Continued)

OTHER PUBLICATIONS

The First Office Action dated May 19, 2020, of counterpart Chinese Application No. 201780023879.3, along with an English translation.

(Continued)

*Primary Examiner* — Mark Kopec
*Assistant Examiner* — Jaison P Thomas
(74) *Attorney, Agent, or Firm* — DLA Piper LLP (US)

(57) ABSTRACT

An electric conductive fiber structure includes an electric conductive resin containing electric conductive polymer(s), the electric conductive resin being filled in gaps between single fibers included in a fiber structure, the electric conductive fiber structure having 15% or more area ratio of the electric conductive resin present in an area of 15 to 30 μm
(Continued)

from a surface when a cross section in a thickness direction of the fiber structure is observed.

11 Claims, 1 Drawing Sheet

(51) Int. Cl.

| | |
|---|---|
| *D06M 15/233* | (2006.01) |
| *D06M 15/63* | (2006.01) |
| *D06M 23/08* | (2006.01) |
| *D06M 15/227* | (2006.01) |
| *H01B 1/12* | (2006.01) |
| *H01B 1/20* | (2006.01) |
| *A61B 5/25* | (2021.01) |
| *A61B 5/291* | (2021.01) |
| *C08L 25/06* | (2006.01) |
| *C08L 67/02* | (2006.01) |
| *C08L 77/00* | (2006.01) |
| *A61B 5/296* | (2021.01) |
| *D06M 101/18* | (2006.01) |
| *D06M 101/32* | (2006.01) |
| *D06M 101/34* | (2006.01) |

(52) U.S. Cl.
CPC .............. *C08L 67/02* (2013.01); *C08L 77/00* (2013.01); *D06M 15/227* (2013.01); *D06M 15/233* (2013.01); *D06M 15/63* (2013.01); *D06M 23/08* (2013.01); *H01B 1/12* (2013.01); *H01B 1/127* (2013.01); *H01B 1/128* (2013.01); *H01B 1/20* (2013.01); *A61B 5/296* (2021.01); *A61B 2562/0209* (2013.01); *A61B 2562/164* (2013.01); *C08L 2203/12* (2013.01); *C08L 2203/20* (2013.01); *C08L 2205/035* (2013.01); *C08L 2205/16* (2013.01); *D06M 2101/18* (2013.01); *D06M 2101/32* (2013.01); *D06M 2101/34* (2013.01)

(58) Field of Classification Search
CPC .......... A61B 2562/164; D06M 15/227; D06M 15/233; D06M 15/63; D06M 23/08; D06M 2101/18; D06M 2101/32; D06M 2101/34; H01B 1/12; H01B 1/20; H01B 1/127; H01B 1/128; C08L 25/06; C08L 67/02; C08L 77/00; C08L 2203/12; C08L 2203/20; C08L 2205/035; C08L 2205/16; C08L 2203/02; C08G 63/183; C08G 63/6886
See application file for complete search history.

(56) References Cited

U.S. PATENT DOCUMENTS

| | | | |
|---|---|---|---|
| 6,228,492 B1 * | 5/2001 | Kinlen | D06M 15/227 264/131 |
| 7,522,951 B2 | 4/2009 | Gough et al. | |
| 2005/0095935 A1 | 5/2005 | Levine et al. | |
| 2012/0148843 A1 | 6/2012 | Levine et al. | |
| 2014/0303470 A1 * | 10/2014 | Tsukada | D06P 1/38 600/377 |
| 2016/0258110 A1 | 9/2016 | Alamer | |
| 2016/0338645 A1 | 11/2016 | Tsukada et al. | |
| 2016/0374615 A1 * | 12/2016 | Tsukada | A61B 5/04085 600/382 |

FOREIGN PATENT DOCUMENTS

| | | |
|---|---|---|
| CN | 101070672 A | 11/2007 |
| CN | 101845753 A | 9/2010 |
| EP | 3 100 677 | 12/2016 |
| JP | 4860155 B2 | 11/2011 |
| JP | 2013-185283 A | 9/2013 |
| JP | 2014-108134 A | 6/2014 |
| JP | 2015-140493 A | 8/2015 |
| TW | 201538131 A | 10/2015 |
| WO | 2005/003446 | 1/2005 |
| WO | 2007/056556 A2 | 5/2007 |
| WO | 2007/056557 | 5/2007 |
| WO | 2013/073673 A1 | 5/2013 |
| WO | 2013/096356 | 6/2013 |
| WO | 2015/115440 A1 | 8/2015 |

OTHER PUBLICATIONS

"Development and Application of Healthy Textiles", 1st Edition, Wang Jinmei et al., China Textile Publishing House, Nov. 2005, p. 253, along with an English translation.
Korean Office Action dated Mar. 30, 2020, of counterpart Korean Application No. 10-2018-7032833, along with an English translation.
Seok-In NA, et al., "Polymer PEDOT:PSS based Transparent Electrode Material Technology", *The Korean Information Display Society*, vol. 11, No. 5, pp. 57-63, along with a Partial English translation.
Ding, Y. et al., "Conductivity Trends of PEDOT~PSS Impregnated Fabric and the Effect of Conductivity on Electrochromic Textile," *ACS Applied Materials & Interfaces*, vol. 2, No. 6, Jun. 23, 2010, pp. 1588-1593.
Rehnby, W. et al., "Coating of Textile Fabrics with Conductive Polymers for Smart Textile Applications," Retrieved from the Internet *Ambiance 08*, (Nov. 17, 2019): URL: https://www.diva-portal.org/smash/get/diva2: 886657/FULLTEXT01.pdf, printout 4 pages.
Shmurak, I. L. et al., "The Effect of the Nature of the Pyridine Groupings on the Adhesion Properties of Vinylpyridine Latexes," *Polymer Science U.S.S.R., Pergamon Press, Oxford*, vol. 8, No. 12, 1966, pp. 2280-2284.
The Supplementary European Search Report dated Nov. 20, 2019, of counterpart European Application No. 17785805.7.
Chilean Office Action dated Dec. 11, 2019, of counterpart Chilean Application No. 2952-2018, along with an English translation.
Notice of Submission of Publications dated Sep. 23, 2020, of counterpart Japanese Application No. 2017-525992, along with an English machine translation.
Submission of Information dated Aug. 31, 2020, of counterpart Japanese Application No. 2017-525992, along with an English machine translation.
Tatsuhiro Horii et al., "Synthesis and Characterization of Highly Conductive PEDOT/PSS Coloidal Gels", *Trans. Mat. Res. Soc.. Japan*, 2012, vol. 37, No. 4, pp. 515-518.
The Website of Mitsui Chemical Analysis & Consulting Service, Inc. "Evaluation of resistance distribution of LiB electrode active material-SSRM", printed on Jul. 10, 2020, URL: https://www.mcanac.co.jp/service/detail/9036.
The web site of UBE Scientific Analysis Laboratory, Inc., "Measurement of resistance distribution by using a spreading resistance microscope", printed on Jul. 10, 2020, URL: https://www.ube-ind.co.jp/usal/documents/s521_900.htm.

* cited by examiner

OBSERVED RANGE: 30 μm×30 μm

HIGH RESISTANCE          LOW RESISTANCE

ELECTRIC CONDUCTIVE FIBER STRUCTURE, ELECTRODE MEMBER, AND METHOD OF PRODUCING ELECTRIC CONDUCTIVE FIBER STRUCTURE

TECHNICAL FIELD

This disclosure relates to an electric conductive fiber structure in which a fiber structure contains an electric conductive resin containing electric conductive polymer(s). Specifically, the disclosure relates to an electric conductive fiber structure that can maintain high electric conductivity even after repeated washing and can even be used for bioelectrodes, an electrode member, and a method of producing an electric conductive fiber structure.

BACKGROUND

Electric conductive fibers have conventionally been known such as fiber of which surfaces coated with metals such as copper, fibers which carbon or metallic thin wires is woven in, and electric conductive fibers obtained by shaping an electric conductive polymer in string form. These electric conductive fibers are used as various types of bioelectrodes used to measure bioelectric signals such as brain waves, electrocardiograms, and electromyograms of humans and animals.

Electric conductive materials such as metals and carbon used in conventional technologies are hydrophobic and hard and thus have a problem in that they are low in adaptability to a use in contact with body surfaces of living bodies which are rich in water and flexible. When bioelectrodes are installed on a body surface, some bioelectrodes formed of a hard, hydrophobic material have difficulty in being brought into intimate contact with the body surface to obtain direct continuity, and therefore electric conductive paste (jelly) that electrically connecting the bioelectrodes and the body surface is required to be used, for example.

Textile-shaped electrodes having electric conductivity are effective as electrodes to be directly attached to body surfaces of living bodies without using any electric conductive paste or the like, and there have been various developments concerned with textile-shaped electrodes. A development is improving electric conductivity by combining a fabric electrode and a water impermeable electric conductive material to reduce the evaporation of water from the fabric electrode, for example (refer to Japanese Patent No. 4860155).

Other developments produce electric conductive polymer fibers by impregnating and/or attaching an aqueous solution of (3,4-ethylenedioxythiophene)-poly(styrene sulfonic acid) (PEDOT-PSS) as an electric conductive polymer particularly excellent in electric conductivity and hydrophilicity as a material having good adaptability to living bodies into/to fibers and using these electric conductive polymer fibers as bioelectrodes and intracorporeal embedded type electrodes (refer to WO 2013/073673).

To create practical electrodes using a textile base, further developments are related to electrode member and a device that can maintain high electric conductivity even after repeated washing and can even be used for bioelectrodes (refer to WO 2015/115440).

However, the electrode part of the fabric electrode disclosed in JP '155 is silicone rubber blended with carbon black or silver powder as an electric conductive material and has a problem in that when it is brought into intimate contact with a body surface for a long time, swelling, rashes or the like occur in living bodies, and it cannot be worn comfortably.

The technique of WO '673 has a problem in that it is poor in practical durability such as washing durability as textile electrodes.

The technique of WO '440 does not take particle diameter of the used electric conductive polymer such as PEDOT-PSS into consideration, and PEDOT-PSS having a large particle diameter is filled in gaps between single fibers of nanofibers in a small amount and supported on the surface of single fibers in a large amount. Consequently, the technique cannot sufficiently use the characteristics of the gaps between single fibers of the nanofibers and is insufficient in practical durability such as washing durability as textile electrodes.

It could therefore be helpful to provide an electric conductive fiber structure having electric conductivity with high practical characteristics, maintains high washing durability and high electric conductivity, and can thus even be used for bioelectrodes by a combination of a fiber structure and an electric conductive resin, an electrode member, and a method of producing an electric conductive fiber structure.

SUMMARY

We thus provide an electric conductive fiber structure including an electric conductive resin containing an electric conductive polymer, the electric conductive resin being filled in gaps between single fibers included in a fiber structure, the electric conductive fiber structure having 15% or more area ratio of the electric conductive resin existence in an area of 15 to 30 µm from a surface when a cross section in a thickness direction of the fiber structure is observed.

The electric conductive resin further contains binder resin(s).

The binder resin is an olefinic resin(s).

Main components of the electric conductive polymer are poly(3,4-ethylenedioxythiophene) and polystyrene sulfonic acid.

The electric conductive fiber structure has antibacterial activity.

The electric conductive fiber structure has an antibacterial activity value of 3 or more by JIS L 1902 (2015 Edition) Bacterial liquid absorption method.

The electric conductive fiber structure includes single fiber(s) of which diameter(s) is/are 10 nm or more and 5,000 nm or less in a part or all.

The electric conductive fiber structure has a surface resistance of $1 \times 10^4 \Omega$ or less after repeating washing 30 times by JIS L 0217 (1995 Edition) 103 method.

An electrode member includes any one of the above-described electric conductive fiber structures for use in acquisition of a biosignal.

A method of producing an electric conductive fiber structure includes a process that an electric conductive resin containing an electric conductive polymer and having a dispersion particle diameter of less than 200 nm is filled in gaps between single fibers included in a fiber structure.

In the method of producing an electric conductive fiber structure, the electric conductive resin contains a mixture of the electric conductive polymer(s) and binder resin(s) as a main component.

A method of producing an electric conductive fiber structure includes a process that an electric conductive resin containing an electric conductive polymer and having an average particle diameter of 20 nm or less is filled in gaps between single fibers included in a fiber structure.

In the method of producing an electric conductive fiber structure, the electric conductive resin contains a mixture of the electric conductive polymer(s) and binder resin(s) as a main component.

We can achieve an electric conductive fiber structure having high performance electric conductivity and flexibility using a textile base and is excellent in washing durability and can thus be used suitably as a textile electrode member acquiring biosignals that is difficult to be developed by conventional electrodes.

DETAILED DESCRIPTION

The following describes an example of an electric conductive fiber structure in detail. This example does not limit the disclosure.

Electric Conductive Fiber Structure

The electric conductive fiber structure contains an electric conductive resin containing (A) electric conductive polymer filled in gaps between single fibers included in a fiber structure and has an area ratio of the electric conductive resin existence in an area of 15 to 30 μm from a surface of 15% or more when a cross section in a thickness direction of the fiber structure is observed in view of electric conductivity, flexibility, and high washing durability. In other words, the electric conductive resin is filled in gaps between single fibers, the electric conductive resin is caused to be impregnated into a deep part, whereby an electric conductive fiber structure having high-performance electric conductivity and flexibility and excellent in washing durability can be obtained. More preferred is that the area ratio is 20% or more, thereby giving excellent durability against repeated washing. The upper limit of the area ratio is preferably 30% in view of flexibility.

(A) Electric Conductive Polymer (A) electric conductive polymer is a blend to impart electric conductivity to the electric conductive fiber structure.

(A) electric conductive polymer is not limited to a particular polymer, and known electric conductive polymers can be used. Specific examples thereof include polythiophene, polypyrrole, polyaniline, polyacetylene, polyphenylenevinylene, polynaphthalene, and derivatives thereof. These may be used alone, or two or more of them may be used in combination. Among them, preferred is an electric conductive polymer containing at least one thiophene ring within the molecule in view of the easiness of forming a highly electric conductive molecule by containing a thiophene ring within the molecule. (A) electric conductive polymer may form a complex with a dopant such as a polyanion.

Among the electric conductive polymer containing at least one thiophene ring within the molecule, poly(3,4-disubstituted thiophene) is more preferred in view of its extreme excellence in electric conductivity and chemical stability. Further, poly(3,4-disubstituted thiophene) is particularly preferably poly(3,4-dialkoxythiophene) or poly(3,4-alkylenedioxythiophene) and most preferably poly(3,4-ethylenedioxythiophene). When the electric conductive polymer is poly(3,4-disubstituted thiophene) or a complex of poly(3,4-disubstituted thiophene) and a polyanion (a dopant), an electric conductive composite material can be formed at low temperatures in a short time, which also provides excellent productivity. The polyanion refers to a dopant of the electric conductive polymer.

The dopant, which is not limited to a particular compound, is preferably a polyanion. Examples of the polyanion include, but are not limited to, carboxylic acid polymers (polyacrylic acid, polymaleic acid, and polymethacrylic acid, for example) and sulfonic acid polymers (polystyrene sulfonic acid, polyvinyl sulfonic acid, and polyisoprene sulfonic acid, for example). These carboxylic acid polymers and sulfonic acid polymers may be copolymers of vinylcarboxylic acids and vinylsulfonic acids and other polymerizable monomers such as acrylates and aromatic vinyl compounds such as styrene and vinylnaphthalene. Among these, polystyrene sulfonic acid is particularly preferred.

(B) Binder Resin

The electric conductive resin preferably further contains a binder resin and is more preferably an electric conductive resin with a mixture of (A) electric conductive polymer and (B) binder resin as a main component.

(B) binder resin contained in the electric conductive polymer is preferably at least one selected from the group consisting of olefinic resins, polyester-based resins, polyurethane, epoxy resins, and acrylic resins. Among them, (B) binder resin is most preferably (B1) olefinic resin in view of bringing blends contained in the electric conductive resin in the electric conductive fiber structure into intimate contact with each other and imparting electric conductivity to the fiber structure more steadily.

(B1) Olefinic Resin (B1) olefinic resin is added to bring blends contained in the electric conductive resin in the electric conductive fiber structure into intimate contact with each other and impart electric conductivity to the fiber structure more steadily. (B1) olefinic resin is preferably (B2) nonpolar olefinic resin in view of the flexibility and washing durability of the obtained fiber structure. "Nonpolar" means having an SP value of 6 to less than 10 and preferably 7 to 9.

(B2) nonpolar olefinic resin is not limited to a particular resin so long as its SP values is 6 to less than 10. (B2) olefinic resin may be used alone, or two or more of them may be used in combination.

Examples of (B1) olefinic resin include polyethylene, polypropylene, cycloolefin polymers (cyclic polyolefins), and polymers obtained by modifying them. For the electric conductive fiber structure, these may be used as (B1) olefinic resin, or olefin-modified products of polyvinyl chloride, polystyrene, or the like may be used as (B1) olefinic resin. These may be used alone, or two or more of them may be used in combination.

Examples of commercially available products that can be used as (B1) olefinic resin include Hardlen (manufactured by Toyobo Co., Ltd.), Aptolok (manufactured by Mitsubishi Chemical Corporation), and Arrowbase (manufactured by Unitika Ltd.).

In the electric conductive fiber structure, the content of (B1) olefinic resin, which is not limited to a particular content, is preferably 0.1 to 1,000 parts by mass and more preferably 5 to 500 parts by mass relative to 100 parts by mass of a solid content of (A) electric conductive polymer. If the content is less than 0.1 part by mass, the strength of the obtained fiber structure may be low; if the content exceeds 1,000 parts by mass, the content of (A) electric conductive polymer in the electric conductive fiber structure is relatively low, and when used as an electrode member, sufficient electric conductivity cannot necessarily be ensured. When the strength of the fiber structure is low, washing durability as a textile electrode may be poor.

In the electric conductive fiber structure, the electric conductive resin may contain other components apart from (A) electric conductive polymer and (B) binder resin. Examples of the other components include (C) electric conductivity improving agent, (D) flexibility imparting agent, (E) surface active agent and/or leveling agent, crosslinking agents, catalysts, and defoaming agents.

(C) Electric Conductivity Improving Agent (C) electric conductivity improving agent may be added to the electric conductive resin. Examples of (C) electric conductivity improving agent include, but are not limited to, compounds having a boiling point of 100° C. or more and having two or more hydroxy groups within the molecule, compounds having a boiling point of 100° C. or more and having at least one sulfinyl group within the molecule, compounds having a boiling point of 60° C. or more and having at least one carbonyl group within the molecule, and compounds having a boiling point of 100° C. or more and having at least one amide group within the molecule. The (C) electric conductivity improving agent may be used alone, or two or more of them may be used in combination.

Examples of the compounds having a boiling point of 100° C. or more and having two or more hydroxy groups within the molecule include ethylene glycol, diethylene glycol, propylene glycol, trimethylene glycol, β-thiodiglycol, triethylene glycol, tripropylene glycol, 1,4-butanediol, 1,5-pentanediol, 1,3-butanediol, 1,6-hexanediol, neopentyl glycol, catechol, cyclohexanediol, cyclohexanedimethanol, glycerin, erythritol, inmatol, lactitol, maltitol, mannitol, sorbitol, xylitol, and sucrose. They may be used alone, or two or more of them may be used in combination.

Examples of the compounds having a boiling point of 100° C. or more and having at least one sulfinyl group within the molecule include dimethylsulfoxide.

Examples of the compounds having a boiling point of 60° C. or more and having at least one carbonyl group within the molecule include acrylic acid, methacrylic acid, methanoic acid, ethanoic acid, propanoic acid, butanoic acid, pentanoic acid, hexanoic acid, octanoic acid, decanoic acid, dodecanoic acid, benzoic acid, p-toluic acid, p-chlorobenzoic acid, p-nitrobenzoic acid, 1-naphthoic acid, 2-naphthoic acid, phthalic acid, isophthalic acid, oxalic acid, malonic acid, succinic acid, adipic acid, maleic acid, and fumaric acid. They may be used alone, or two or more of them may be used in combination.

Examples of the compounds having a boiling point of 100° C. or more and having at least one amide group within the molecule include N,N-dimethylacetamide, N-methylformamide, N—N-dimethylformamide, acetamide, N-ethylacetamide, N-phenyl-N-propylacetamide, and benzamide. They may be used alone, or two or more of them may be used in combination.

When the electric conductive resin contains (C) electric conductivity improving agent, the content thereof, which is not limited to a particular content, is preferably 0.01 to 100,000 parts by mass and more preferably 0.1 to 10,000 parts by mass relative to 100 parts by mass of (A) electric conductive polymer. If the content of (C) electric conductivity improving agent is less than 0.01 part by mass, a sufficient electric conductivity improving effect cannot necessarily be obtained. If the content exceeds 100,000 parts by mass, the drying performance of the fiber structure may degrade.

(D) Flexibility Imparting Agent (D) flexibility imparting agent may be added to the electric conductive resin. Examples of (D) flexibility imparting agent include, but are not limited to, glycerol, sorbitol, polyglycerin, polyethylene glycol, and a polyethylene glycol-polypropylene glycol copolymer. They may be used alone, or two or more of them may be used in combination.

When the electric conductive resin contains (D) flexibility imparting agent, the content thereof, which is not limited to a particular content, is preferably 10 to 10,000 parts by mass and more preferably 100 to 5,000 parts by mass relative to 100 parts by mass of (A) electric conductive polymer. If the content of (D) flexibility imparting agent is less than 10 parts by mass, sufficient flexibility cannot necessarily be obtained. If the content exceeds 10,000 parts by mass, the fiber structure may degrade in electric conductivity and/or strength or may significantly degrade in washing durability.

(E) Surface Active Agent/Leveling Agent (E) surface active agent/leveling agent may be added to the electric conductive resin. In the electric conductive fiber structure, one compound may correspond to both the surface active agent and the leveling agent. When the surface active agent and the leveling agent are different compounds, the surface active agent and the leveling agent may be used in combination.

The surface active agent is not limited to a particular compound so long as it has a leveling improving effect. Specific examples thereof include siloxane-based compounds such as polyether-modified polydimethylsiloxane, polyether-modified siloxane, polyetherester-modified hydroxy group-containing polydimethylsiloxane, polyether-modified acrylic group-containing polydimethylsiloxane, polyester-modified acrylic group-containing polydimethylsiloxane, perfluoro-polydimethylsiloxane, perfluoropolyether-modified polydimethylsiloxane, and perfluoropolyester-modified polydimethylsiloxane; fluorine-containing organic compounds such as perfluoro-alkyl carboxylic acids and perfluoro-alkyl polyoxyethylene ethanol; polyether-based compounds such as polyoxyethylene alkylphenyl ethers, propylene oxide polymers, and ethylene oxide polymers; carboxylic acids such as amine salts of coconut fatty acid and gum rosin; ester-based compounds such as castor oil sulfuric esters, phosphoric esters, alkylether sulfates, sorbitan fatty acid esters, sulfonic acid esters, and succinic acid esters; sulfonate compounds such as amine salts of alkylaryl sulfonic acids and sodium dioctyl sulfosuccinate; phosphate compounds such as sodium lauryl phosphate; amid compounds such as coconut fatty acid ethanol amide; and acrylic-based compounds. The surface active agents may be used alone, or two or more of them may be used in combination. Among them, preferred are siloxane-based compounds and fluorine-containing organic compounds in view of significantly obtaining the leveling improving effect.

The leveling agent is not limited to a particular compound. Examples thereof include siloxane-based compounds such as polyether-modified polydimethylsiloxane, polyether-modified siloxane, polyetherester-modified hydroxy group-containing polydimethylsiloxane, polyether-modified acrylic group-containing polydimethylsiloxane, polyester-modified acrylic group-containing polydimethylsiloxane, perfluoro-polydimethylsiloxane, perfluoropolyether-modified polydimethylsiloxane, and perfluoropolyester-modified polydimethylsiloxane; fluorine-containing organic compounds such as perfluoro-alkyl carboxylic acids and perfluoro-alkyl polyoxyethylene ethanol; polyether-based compounds such as polyoxyethylene alkylphenyl ethers, propylene oxide polymers, and ethylene oxide polymers; carboxylic acids such as amine salts of coconut fatty acid and gum rosin; ester-based compounds such as castor oil sulfuric esters, phosphoric esters, alkylether sulfates, sorbitan fatty acid esters, sulfonic acid esters, and succinic acid esters; sulfonate compounds such as amine salts of alkylaryl sulfonic acids and sodium dioctyl sulfosuccinate; phosphate compounds such as sodium lauryl phosphate; amid compounds such as coconut fatty acid ethanol amide; and acrylic-based compounds. The leveling agents may be used alone, or two or more of them may be used in combination.

Method of Producing Electric Conductive Fiber Structure

The electric conductive fiber structure is obtained by causing an electric conductive resin with a mixture of an electric conductive polymer and an olefinic resin as a main component to be filled in gaps between single fibers included in a fiber structure. For the electric conductive resin caused to be supported, one having a small particle diameter is used.

When being caused to be supported, the electric conductive resin is preferably caused to be supported in the form of a dispersion liquid or a solution of the electric conductive resin. Both an entity that completely dissolves all the components contained in the electric conductive resin (that is a "solvent") and an entity that disperses insoluble components (that is, a "dispersion medium") are referred to as a "solvent" without any distinction. The following describes the solvent.

Solvent

Examples of the solvent include, but are not limited to, water; alcohols such as methanol, ethanol, 2-propanol, 1-propanol, and glycerin; ethylene glycols such as ethylene glycol, diethylene glycol, triethylene glycol, and tetraethylene glycol; glycol ethers such as ethylene glycol monomethyl ether, diethylene glycol monomethyl ether, ethylene glycol diethyl ether, and diethylene glycol dimethyl ether; glycol ether acetates such as ethylene glycol monoethyl ether acetate, diethylene glycol monoethyl ether acetate, and diethylene glycol monobutyl ether acetate; propylene glycols such as propylene glycol, dipropylene glycol, and tripropylene glycol; propylene glycol ethers such as propylene glycol monomethyl ether, propylene glycol monoethyl ether, dipropylene glycol monomethyl ether, dipropylene glycol monoethyl ether, propylene glycol dimethyl ether, dipropylene glycol dimethyl ether, propylene glycol diethyl ether, and dipropylene glycol diethyl ether; propylene glycol ether acetates such as propylene glycol monomethyl ether acetate, propylene glycol monoethyl ether acetate, dipropylene glycol monomethyl ether acetate, and dipropylene glycol monoethyl ether acetate; tetrahydrofuran; acetone; and acetonitrile. The solvents may be used alone, or two or more of them may be used in combination.

The solvent is preferably water or a mixture of water and organic solvents. When the electric conductive fiber structure contains water as the solvent, the content of water, which is not limited to a particular content, is preferably 20 to 1,000,000 parts by mass and more preferably 200 to 500,000 parts by mass relative to 100 parts by mass of the solid content of (A) electric conductive polymer. If the content of water is less than 20 parts by mass, viscosity increases, which may make handling difficult. If the content of water exceeds 1,000,000 parts by mass, the concentration of the electric conductive fiber structure is extremely low, which may increase the amount of liquid used.

The electric conductive resin is supported on the fiber structure using a normal method such as immersion, coating, or spraying, and the fiber structure supporting the electric conductive resin is heated to obtain an electric conductive fiber structure.

In view of enabling the electric conductive resin to be filled in gaps between single fibers included in the fiber structure in a large amount, immersion and coating are preferred.

Particle Diameter of Electric Conductive Resin

The dispersion particle diameter of the electric conductive resin with (A) electric conductive polymer or the mixture of (A) electric conductive polymer and (B) binder resin as a main component is preferably less than 200 nm. If the dispersion particle diameter of the electric conductive resin is 200 nm or more, the electric conductive resin is difficult to be filled in gaps between single fibers of fibers included in the fiber structure and is supported on the surface of single fibers in a large amount, which is easily peeled off by physical impact, and high electric conductivity after repeated washing cannot be maintained. If the dispersion particle diameter of the electric conductive resin is less than 200 nm, the electric conductive resin is supported on the surface of single fibers and gaps between single fibers in a large amount and is little peeled off by physical impact, and high electric conductivity after repeated washing can be maintained.

Whether the dispersion particle diameter is less than 200 nm is measured by filtering the electric conductive resin dispersed in a dispersion liquid of the electric conductive resin with a syringe filter with a pore diameter of 0.2 μm. In other words, it can be determined that the dispersion particle diameter is less than 200 nm if the electric conductive resin dispersed in the dispersion liquid of the electric conductive resin passes through the syringe filter.

The average particle diameter of the electric conductive resin with (A) electric conductive polymer or the mixture of (A) electric conductive polymer and (B) binder resin as a main component is preferably 20 nm or less. With this average particle diameter, the electric conductive resin is supported on the surface of single fibers and gaps between single fibers in a larger amount and is particularly little peeled off by physical impact, and high electric conductivity after repeated washing can be maintained to a larger extent.

The average particle diameter of the electric conductive resin refers to a median diameter (D50) when measured by dynamic light scattering.

Using the electric conductive resin containing (A) electric conductive polymer or (A) electric conductive polymer and (B) binder resin, with the dispersion particle diameter being 200 nm or less or with the average particle diameter being 20 nm or less, the electric conductive resin is filled in gaps between single fibers of fibers included in the fiber structure, whereby the electric conductive resin can be impregnated into a deep part of the fiber structure. With this impregnation, an electric conductive fiber structure excellent in durability against repeated washing can be obtained.

Denatron FB408B, Denatron TX401 (manufactured by Nagase Chemtex Corporation) and the like are commercially available as a dispersion liquid that disperses an electric conductive resin with a mixture of (A) electric conductive polymer with poly(3,4-ethylenedioxythiophene) and polystyrene sulfonic acid as main components and (B1) olefinic resin as (B) binder resin as a main component in a solvent, which can be used as the electric conductive resin of the electric conductive fiber structure.

In view of improving electric conductivity and stability of the electric conductive fiber structure, glycerol, a physiological saline solution or the like is further imparted to the fiber structure containing the electric conductive resin, which can be suitably used. The electric conductive fiber structure is not limited to these examples. The exemplified electric conductive resins are imparted to the fiber structure using a known method such as immersion, coating, or spraying, whereby the electric conductive resin is supported on the surface of single fibers included in the fiber structure and gaps between single fibers, and a continuous layer of the electric conductive resin can be formed.

Fiber Structure

In the electric conductive fiber structure, the form of fibers included in the fiber structure may be any of a monofilament yarn, a multifilament yarn, and a staple yarn. The cross-sectional shape of the fibers may be a circular cross section, a triangular cross section, or other modified cross sections with a high modification degree and is not limited to a particular shape.

A polymer as a material of the fibers included in the fiber structure is not limited to a particular polymer so long as it is a polymer that can be formed into fibers by a known method and refers to, but are not limited to, polyolefin-based fibers with polyethylene, polypropylene or the like as a main component, cellulose for chemical fibers such as rayon and acetate, and polymers for synthetic fibers such as polyester and nylon.

In the electric conductive fiber structure, the fineness of the fibers included in the fiber structure is preferably uniform and fine size. In melt spinning, particularly preferably exemplified is a fiber formed of a thermoplastic polymer that enables composite spinning, especially polyester.

Examples of the polyester referred to in this context include polyesters with terephthalic acid as a main acid component and with an alkylene glycol with a carbon atom number of 2 to 6, that is, at least one glycol selected from ethylene glycol, trimethylene glycol, tetramethylene glycol, pentamethylene glycol, and hexamethylene glycol, preferably ethylene glycol and tetramethylene glycol, and particularly preferably ethylene glycol as a main glycol component.

The polyester may be a polyester with a mixture of terephthalic acid and another bifunctional carboxylic acid as an acid component and may be a polyester with a mixture of the above glycol and another diol component as a glycol component. Further, the polyester may be a polyester with a mixture of terephthalic acid and another bifunctional carboxylic acid as an acid component and with a mixture of the above glycol and another diol component as a glycol component.

Examples of the other bifunctional carboxylic acid apart from terephthalic acid used in this example include aromatic, aliphatic, and alicyclic bifunctional carboxylic acids such as isophthalic acid, naphthalene dicarboxylic acid, diphenyldicarboxylic acid, diphenoxyethanedicarboxylic acid, adipic acid, sebacic acid, and 1,4-cyclohexanedicarboxylic acid. Examples of the diol compound apart from the above glycol include aromatic, aliphatic, and alicyclic diol compounds such as cyclohexane-1,4-dimethanol, neopentyl glycol, bisphenol A, and bisphenol S.

The polyester used as fibers included in the fiber structure may be synthesized by any method. Polyethylene terephthalate, for example, can be normally manufactured by a first-step reaction that produces a glycol ester of terephthalic acid and/or its oligomer by directly subjecting terephthalic acid and ethylene glycol to an esterification reaction, by subjecting a lower alkyl ester of terephthalic acid such as dimethyl terephthalate and ethylene glycol to an ester exchange reaction, or by reacting terephthalic acid and ethylene oxide and a second-step reaction that heats the reaction product in the first step under reduced pressure to be subjected to a polycondensation reaction until a desired degree of polymerization is gained.

The form of the fiber structure may be a mesh, paper, a woven fabric, a knitted fabric, a nonwoven fabric, a ribbon, a string, or the like, which may be any form corresponding to a purpose and is not limited to a particular form.

The fiber structure includes multifilament yarns, and an electric conductive material is preferably supported on the surface of single fibers included in the multifilament yarns and filled in gaps between single fibers.

In view of supporting the electric conductive resin on the fiber structure and high electric conductivity of the electric conductive fiber structure, the fiber structure preferably includes multifilament yarns including a plurality of single fibers. The fineness of the multifilament yarns, which is not limited to a particular value, is preferably 30 dtex to 400 dtex in view of using the characteristics as the fiber structure. The mixing ratio of the multifilament yarns in the fiber structure is not limited to a particular ratio to the extent that the performance is not affected. A higher mixing ratio is preferred in view of making it easier for the electric conductive resin to be supported and improving practical durability. The used multifilament yarns can be subjected to thread-plying, doubling, and crimping by known methods.

The multifilaments included in the fiber structure further preferably include single fibers with 0.2 dtex or less. In view of supporting the electric conductive polymer on the fiber structure and high electric conductivity, a fiber structure with a small fiber diameter of single fibers is desirable and preferably includes single fibers with 0.2 dtex or less. For polyethylene terephthalate with a density of 1.38 g/cm$^3$ as an example, a fineness of 0.2 dtex forms microfibers with a fiber diameter of about 5 μm. With a density of a polymer compound capable of forming fibers and microfibers with 0.2 dtex or less, they are fibers with sufficiently small fineness, and many gaps can be formed from single fibers.

A larger number of single fibers included in the multifilaments fractionate gaps formed from a plurality of single fibers, that is, parts on which the electric conductive resin is supported and increase the supportability of the electric conductive resin on the fiber structure. In addition, the fiber diameter of the single fibers is reduced, whereby even when the parts that can support the electric conductive resin are fractionated, the continuity of the electric conductive resin is maintained, and high electric conductivity can be simultaneously exhibited.

For microfibers with a large number of single fibers, sea-island type composite fibers formed of two kinds of polymers having different solubility are prepared, and one component of the sea-island type composite fibers is removed with a solvent to form ultrafine fibers, for example. Although the respective thicknesses of island components and the distribution thereof are not fixed, the constituent number of the island components is increased, whereby multifilaments formed of microfibers can be formed.

In the multifilaments that can be manufactured by the above method, the constituent number of the island components of the microfibers, which relates to monofilament fineness or the presence or absence of thread plying to single fibers, is 5 or more, preferably 24 or more, and further preferably 50 or more. Further, denier mix is also included. The cross-sectional form of the entire multi-component fibers is not limited to a circular hole and includes various known fiber cross sections such as trilobal type, tetralobal type, T type, and hollow type ones.

One preferred form of the fiber structure is obtained by treating a woven fabric woven using the sea-island type composite fibers by a method such as chemical peeling, physical peeling, or removal by dissolution to manufacture a woven or knitted fabric with the constituent fibers made ultrafine, and entangling the fibers by water jet punching or the like.

In the preferred form of the fiber structure described above, to maintain the fiber entangled structure, a polymer elastic substance such as polyurethane is imparted by means such as impregnation. With this treatment, an effect of improving the dyeability, the size stability, the quality stability and the like of the fiber structure is produced. Further, the surface of the sheet-shaped fiber structure is napped to form erected fibers formed of a bundle of ultrafine fibers on the surface, whereby various types of sheet-shaped products corresponding to an object can be made.

On the fiber structure, in addition to fiber entanglement and napping, many pieces of processing such as shrinking treatment, form fixing treatment, compressing treatment, dyeing finishing treatment, oil imparting treatment, thermal fixing treatment, solvent removal, form fixing agent removal, combing treatment, brightening treatment, flat (roll) pressing treatment, and high-performance short-cut shirring treatment (cutting of erected fibers) are performed in combination as appropriate at each process. They are performed in an unlimited manner so long as the performance as an electrode is not impaired.

Further, in the fiber structure, at least part of the single fibers are further preferably nanofibers with a single fiber diameter of 10 nm or more and 5,000 nm or less. Suitably used are fiber structures including multifilament yarns including nanofibers prepared by known methods such as a nanofiber staple yarn aggregate manufactured from "Nanoalloy (registered trademark)" fibers and an aggregate of monofilaments manufactured by an electrospinning method or the like.

The multifilament yarns including nanofibers can be manufactured by a known composite spinning method or the like. As an example, effectively used are nanofiber multifilament yarns with small variations in fiber diameter obtained by removing the sea component from composite fibers using a composite spinneret exemplified in Japanese Patent Application Laid-open No. 2013-185283. This is not limiting.

The weight per unit area of the electric conductive fiber structure is preferably 50 g/m$^2$ or more and 300 g/m$^2$ or less. If the weight per unit area is less than 50 g/m$^2$, the raw fabric is extremely thin, and the amount of impregnation of the electric conductive resin is small. If the weight per unit area exceeds 300 g/m$^2$, it is extremely thick, which causes a feel of wearing to degrade. The weight per unit area is more preferably 100 g/m$^2$ or more and 250 g/m$^2$ or less.

The electric conductive fiber structure preferably has an antibacterial activity value of *Staphylococcus aureus* as human indigenous bacteria of 3 or more by JIS L 1902 (2015 Edition) Bacterial liquid absorption method. If the antibacterial activity value is less than 3, when an electrode member including the electric conductive fiber structure is installed on clothes, for example, the propagation of bacteria caused by perspiration cannot be reduced, and when the clothes after perspiring are left as they are, the clothes emit odors by the propagation of bacteria. An electrode member including the electric conductive fiber structure with an antibacterial activity value of 3 or more can reduce the propagation of bacteria caused by perspiration and can reduce the emission of odors.

The electric conductive fiber structure preferably has a surface resistance after repeating washing 30 times by JIS L 0217 (1995 Edition) 103 method is $1\times10^4 \Omega$ or less. The electrode member can be washed in homes, although it includes the fiber structure and the electric conductive resin. A larger number of single fibers included in the fiber structure fractionate gaps formed from a plurality of single fibers, that is, parts on which the electric conductive resin is supported, increase the supportability of the electric conductive resin with a dispersion particle diameter of 200 nm or less or with an average particle diameter of 20 nm or less on the fiber structure, and can impart high washing durability.

When the electric conductive fiber structure is used as a bioelectrode, high air-permeability is required in view of adhesion and followability to skin or to achieve a flexible, soft feel and reduce sweatiness and rashes caused by perspiration on skin, and the form of the fiber structure is preferably the shape of a woven fabric, a knitted fabric, and a nonwoven fabric.

For the fiber structure, dyeing, functional treatment and the like by known methods and means are performed in an unlimited manner so long as the performance as an electrode is not impaired. Surface physical treatment such as napping of the surface of the electrode member, calendering, embossing, or water jet punching are also performed in an unlimited manner so long as the performance as an electrode is not impaired.

The shape and size of the electrode member are not set to particular ones so long as biosignals can be detected.

In the electrode member including the electric conductive fiber structure, a resin layer may be laminated on one side of the fiber structure containing the electric conductive resin.

Examples of preferred use modes of the electric conductive fiber structure include being in direct contact with living bodies to enable electric signals to be acquired and/or electric signals to be imparted, which include electrode members of cardiac potential, myoelectric potential, brain waves and the like acquiring electric signals from living bodies and electrode members of low frequency, high frequency, EMS, and the like imparting electric stimuli to living bodies. Examples include, but are not limited to, single bodies of fibers, fabrics, films, slit yarns, unwoven fabrics, resins, and structures formed of composites thereof. Examples of further specific shapes include, but are not limited to, ones in direct contact with skin such as electrodes formed of the base, electric wires, wear, underpants, gloves, socks, brassieres, headbands, wristbands, mufflers, caps, belly bands, athletic supporters, shoes, sheets, glasses, hairbands, hair ornament adhesive members, headphones, watches, chairs, toilet seats, handles, beds, carpets, and various kinds of covers.

For an electrode, an electrode by itself and/or a combination with the above members in direct contact with skin can also be suitably used. The shape of the electrode by itself is not limited to a circle, a polygon and the like.

The size of the electrode is only required to have a contact area enabling a desired biosignal to be acquired and is not limited. To improve adhesion to living bodies, a general flat electrode may have a three-dimensional structure such as a loop shape or be swelled by air to follow movement.

When being used as an electrode in combination with other structures such as clothes to acquire an electric signal at a desired part, the fiber structure can also be suitably used with a shape attachable and detachable to and from clothes using buttons, hooks, magnets, and Magic Tape (registered trademark) in combination.

The electric conductive fiber structure can also be used as a planer heating element, is excellent in flexibility and flex resistance, is light in weight, can be reduced in thickness, and can thus be used as a fabric heater.

EXAMPLES

The following describes the electric conductive fiber structure in detail by examples. These examples do not limit the electric conductive fiber structure. Measured values in the examples and comparative examples were obtained by the following methods.

(1) Electric Conductive Resin Impregnation Area Ratio

The area ratio of the electric conductive resin existence in an area of 15 to 30 µm from a surface when a cross section in the thickness direction of the electric conductive fiber structure was observed (an electric conductive resin impregnation area ratio) was determined as follows.

Using an argon (Ar)-ion beam processing apparatus, the electric conductive fiber structure was cut in the thickness direction to prepare a cross-sectional thin film piece to obtain a sample for measurement. For the obtained sample for measurement, using scanning spreading resistance microscopy (hereinafter, referred to as SSRM), voltage was applied from the back side of the sample for measurement, and using an electric conductive probe, the presence or absence of the continuity of the surface layer of the sample was observed. In an observed image, as illustrated in a cross-sectional image of FIG. 1 below, a 30 µm×30 µm square area was set such that the highest part of the surface layer part of the fiber structure was in contact with the upper part of a field of view. For a 15 µm×30 µm area at 15 µm below the highest position of the surface part, using image processing software (GIMP 2.8 portable), with a threshold value set at 60, an area ratio impregnated with the electric conductive resin in an area of 15 to 30 µm from the surface in the thickness direction of the electric conductive fiber structure was determined. In this process, the number of observation was 20 cross sections extracted at random. The average value of the respective area ratios determined at the 20 places was calculated, which was defined as a "electric conductive resin impregnation area ratio."

Observation apparatus: manufactured by Bruker AXS and Digital Instruments
 NanoScope IVa AFM
 Dimension 3100 stage AFM system
 +SSRM option
 SSRM scanning mode: simultaneous measurement of contact mode and spreading resistance
 SSRM probe (Tip): diamond-coated silicon cantilever
 Probe product name: DDESP-FM (manufactured by Bruker AXS)
 Ar-ion beam processing apparatus: IM-4000 manufactured by Hitachi High-Technologies Corporation
 Acceleration voltage: 3 kV (2) Fineness The fineness of the sea-island type composite fibers included in the fiber structure was calculated by immersing a fabric in a 3% by mass aqueous sodium hydroxide solution (75° C., with a bath ratio of 1:30) to remove an easily soluble component by 99% or more, dissolving yarns, extracting a multifilament formed of ultrafine fibers, measuring the mass of 1 meter of this multifilament, and multiplying the mass by 10,000. This procedure was repeated ten times, and a value obtained by rounding off their simple average to the first decimal place was defined as fineness.

For other fibers, fineness was calculated by dissolving yarns, extracting a multifilament, measuring the mass of 1 meter of this multifilament, and multiplying the mass by 10,000. This procedure was repeated ten times, and a value obtained by rounding off their simple average to the first decimal place was defined as fineness.

(3) Fiber Diameter

Multifilaments extracted from fibers were embedded in epoxy resin, were frozen with FC4E Cryosectioning System manufactured by Reichert Inc., and were cut with Reichert-Nissei ultracut N (an ultramicrotome) equipped with a diamond knife, and their cut faces were photographed with model VE-7800 scanning electron microscope (SEM) manufactured by Keyence Corporation with a magnification of 5,000 times for nanofibers, 1,000 times for microfibers, and 500 times for others. From an obtained photograph, 150 ultrafine fibers selected at random were extracted, and for the photograph, all circumscribed circle diameters (fiber diameters) were measured using image processing software (WINROOF).

(4) Variations in Fiber Diameter (CV % (A))

The average fiber diameter and the fiber diameter standard deviation of the fiber diameter measured in (3) were determined, and variations in fiber diameter (CV % (A): coefficient of variation) was calculated on the basis of the following expression. For all of the above values, measurements were performed at three places for each photograph to determine averages of the three places; the averages were measured to the first decimal place in mm and were rounded off to the nearest integers.

Variations in fiber diameter ($CV\%$ ($A$))=(the fiber diameter standard deviation/the average fiber diameter)×100

(5) Modification Degree and Variations in Modification Degree (CV % (B))

Cross sections of multifilaments were photographed in a way similar to that for the fiber diameter in (3); from each of those images, the diameter of a perfect circle circumscribed to a cut face was defined as a circumscribed circle diameter (a fiber diameter), the diameter of a perfect circle inscribed thereto was defined as an inscribed circle diameter, and a modification degree=the circumscribed circle diameter/the inscribed circle diameter was determined to the third decimal place, which was rounded off to the second decimal place to be determined to be the modification degree. This modification degree was measured for 150 ultrafine fibers extracted at random within the same image, and from its average and standard deviation, variations in modification degree (CV % (B): coefficient of variation) was calculated on the basis of the following expression. The variations in modification degree was rounded off to the first decimal place.

Variations in modification degree ($CV\%$ ($B$))=(the standard deviation of the modification degree/ the average of the modification degree)×100(%)

(6) Weight Per Unit Area

For an electrode base fabric, a weight per unit area in the standard state of JIS L 1096 (Testing methods for general woven fabrics) (1999) and JIS L 1018 (Testing methods for knitted fabrics) (1999) was measured.

(7) Dispersion Particle Diameter of Electric Conductive Resin

The electric conductive resin dispersed in a dispersion liquid was filtered with a Minisart 0.2 µm syringe filter manufactured by Sartorius to determine whether the dispersion particle diameter of the electric conductive resin was less than 200 nm.

(8) Average Particle Diameter of Electric Conductive Resin (Dynamic Light Scattering)

A hydrodynamic diameter was calculated from particle diameter distribution determined by measuring the electric conductive resin diluted by 50 times obtained by adding 1 g of the electric conductive resin to 49 g of water with stirring with NanotracWave series manufactured by Microtrac, which was defined as an average particle diameter.

(9) Electric Conductive Resin Adhesion Amount

An electric conductive resin adhesion amount was measured from a mass change of a fiber structure as a test fabric before and after application of an electric conductive resin dispersion liquid at the standard state (20° C.×65% RH). The calculation expression was as follows:

The electric conductive resin adhesion amount ($g/m^2$)=(the mass of the test fabric after treatment (g)–the mass of the test fabric before treatment)/the area of the test fabric on which the dispersion liquid has been applied ($m^2$)

(10) Surface Resistance

With a 10 cm×10 cm electric conductive fiber structure as a test piece, it was placed on high-quality expanded polystyrene, and its surface resistance value (Ω) was measured under an environment of 20° C. and 40% RH using a resistance meter (four-probe resistance meter Loresta-AX MCP-T370 manufactured by Mitsubishi Chemical Analytech Co., Ltd.).

(11) Washing Durability

With a 10 cm×10 cm electric conductive fiber structure as a test piece, a surface resistance value after washing by a 30-times repeating method was measured by a method in conformity with JIS L 0217 (1995) 103 method. For the washing machine, a fully automatic washing machine (National NA-F50Z8) was used.

(12) Bending Resistance

The bending resistance of the electric conductive fiber structure was measured in conformity with JIS L 1096 (Testing methods for woven and knitted fabrics) (1999) Bending resistance A method (45° cantilever method).

(13) Presence or Absence of Peeling of Electric Conductive Resin

General adhesive tape cut into 25 mm wide and 50 mm long was pasted on a 10 cm×10 cm test piece of the electric conductive fiber structure and was peeled off with a constant force, and the presence or absence of the peeling of the electric conductive resin was visually observed. The absence of peeling is indicated by A, whereas the presence of peeling is indicated by B.

(14) Antibacterial Activity

The antibacterial activity of the fiber structure having electric conductivity was measured in conformity with JIS L 1902 Testing methods for antibacterial activity on fiber products (2015) Bacterial culture absorption method. *Staphylococcus aureus* was used as a test strain.

The following describes examples and comparative examples of the electric conductive fiber structure.

Example 1

Figure 1:
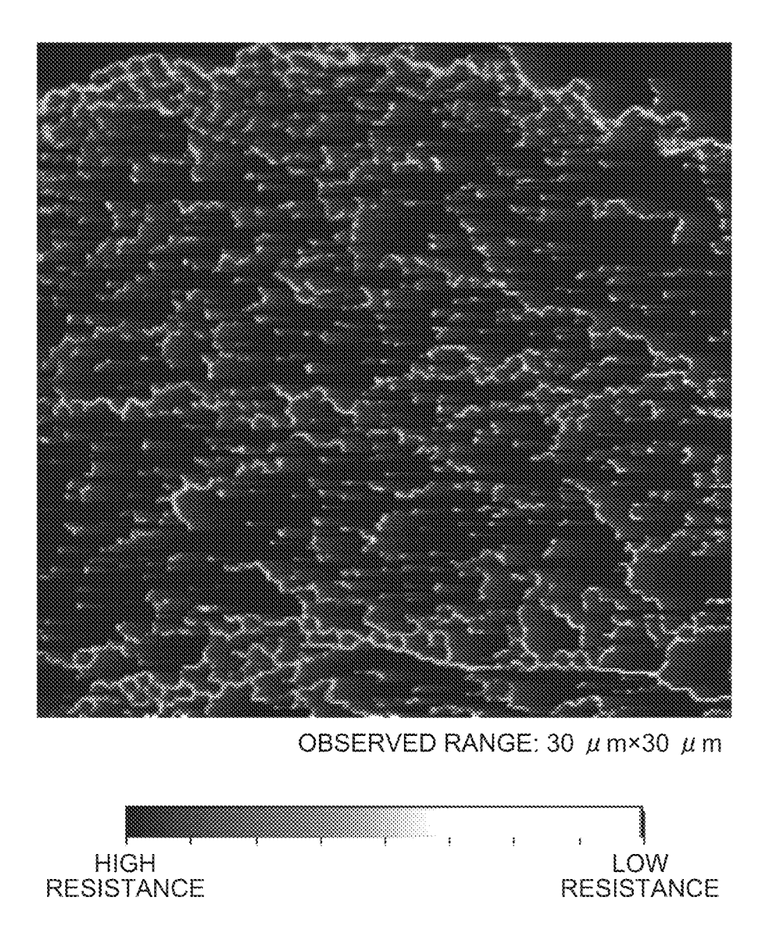
The Drawing is a photograph of an electric conductive fiber structure observed with a scanning probe microscope.

Using 100T-136F polyester nanofiber combined filament yarns obtained by combining 75T-112F (with a sea-island ratio of 30%:70% and an island number of 127/Filament) nanofibers of an alkaline hot water-soluble polyester formed of polyethylene terephthalate as an island component and a polyester having a copolymer of terephthalic acid and 5-sodium sulfoisophthalic acid as acid components as a sea component and 22T-24F highly shrinkable yarns, a circularly knitted fabric was knitted with a smooth texture. Next, the fabric was immersed in a 3% by mass aqueous sodium hydroxide solution (75° C., with a bath ratio of 1:30) to remove an easily soluble component, and a nanofiber-highly shrinkable yarn combined yarn-used knitted fabric was obtained. "Denatron FB408B" (manufactured by Nagase Chemtex Corporation) as an electric conductive resin-containing dispersion liquid was applied to the obtained knitted fabric as a fiber structure to give an agent application amount of 15 $g/m^2$ by a known knife coating method and was heated at 120° C. to 130° C. to obtain an electric conductive fiber structure. Table 1 lists the used materials and the characteristics of the obtained electric conductive fiber structure. FIG. 1 illustrates a cross-sectional photograph used for the evaluation of the electric conductive resin impregnation area ratio of the electric conductive fiber structure according to Example 1. FIG. 1 reveals that low resistance is present, that is, the electric conductive resin is impregnated from a surface to 30 µm.

Example 2

The same processing as that of Example 1 was performed except that the electric conductive resin-containing dispersion liquid was changed from "Denatron FB408B" to "Denatron TX401" to manufacture an electric conductive fiber structure. Table 1 lists the used materials and the characteristics of the obtained electric conductive fiber structure.

Example 3

The same processing as that of Example 1 was performed except that the highly shrinkable yarns were changed from 22T-24F to 33T-6F to make 110T-118F polyester nanofiber combined filament yarns combined with 75T-112F (with a sea-to-island ratio of 30%:70% and an island number of 127/Filament) as the nanofibers and that dyeing treatment was performed to manufacture an electric conductive fiber structure. Table 1 lists the used materials and the characteristics of the obtained electric conductive fiber structure.

Example 4

The same processing as that of Example 1 was performed except that the fabric structure was changed from the knitted fabric to a plain-woven fabric to manufacture an electric conductive fiber structure. Table 1 lists the characteristics of the used materials and the characteristics of the obtained electric conductive fiber structure.

Example 5

The same processing as that of Example 1 was performed except that the 22T-24F highly shrinkable yarns were not used and that the polyester nanofiber combined filament yarns were changed to 75T-112F (with a sea-island ratio of 30%:70% and an island number of 127/Filament) polyester nanofiber single yarns to manufacture an electric conductive fiber structure. Table 1 lists the characteristics of the used materials and the characteristics of the obtained electric conductive fiber structure.

Example 6

The same processing as that of Example 1 was performed except that the 22T-24F highly shrinkable yarns were not used and that 75T-112F (with a sea-island ratio of 30%:70% and an island number of 127/Filament) was changed to 100T-30F (with a sea-island ratio of 30%:70% and an island number of 2,048/Filament) polyester nanofiber single yarns to manufacture an electric conductive fiber structure. Table 1 lists the characteristics of the used materials and the characteristics of the obtained electric conductive fiber structure.

Example 7

The same processing as that of Example 1 was performed except that the 22T-24F highly shrinkable yarns were not used and that 75T-112F (with a sea-island ratio of 30%:70% and an island number of 127/Filament) was changed to 120T-60F (with a sea-island ratio of 50%:50% and an island number of 2,048/Filament) polyester nanofiber single yarns to manufacture an electric conductive fiber structure. Table 1 lists the used materials and the characteristics of the obtained electric conductive fiber structure.

Example 8

The same processing as that of Example 1 was performed except that the 22T-24F highly shrinkable yarns were not used and that the polyester nanofiber combined filament yarns were changed to 75T-112F (with a sea-island ratio of 30%:70% and an island number of 127/FILAMENT) triangular-cross-section polyester nanofiber single yarns to manufacture an electric conductive fiber structure. Table 1 lists the used materials and the characteristics of the obtained electric conductive fiber structure.

Example 9

The same processing as that of Example 1 was performed except that the 22T-24F highly shrinkable yarns were not used and that 75T-112F (with a sea-island ratio of 30%:70% and an island number of 127/Filament) was changed to a 66T-9F (with a sea-island ratio of 20%:80% and an island number of 70/Filament) microfiber woven fabric to manufacture an electric conductive fiber structure. Table 1 lists the used materials and the characteristics of the obtained electric conductive fiber structure.

Example 10

A needle punched nonwoven fabric formed using polymer arrangement fibers (with a sea-island ratio of 57%:43% and an island number of 16) with 4.2 dtex, a length of 51 mm, polyethylene terephthalate as an island component, and polystyrene as a sea component was impregnated with polyurethane and was subjected to wet solidification. The content of polyurethane was 49% relative to the mass of polyethylene terephthalate. This nonwoven fabric was immersed in trichloroethylene and was squeezed with a mangle to remove a polystyrene component to obtain ultrafine fibers with a monofilament fineness of 0.15 dtex. With a buffing machine, a nonwoven fabric with fluffing processing and dyeing treatment performed was obtained. Next, similarly to Example 1, "Denatron FB408B" (manufactured by Nagase Chemtex Corporation) as an electric conductive resin-containing dispersion liquid was applied to the obtained nonwoven fabric as a fiber structure to give an agent application amount of 15 g/m$^2$ by a known knife coating method to obtain an electric conductive fiber structure. Table 1 lists the used materials and the characteristics of the obtained electric conductive fiber structure.

Example 11

Using 100T-136F polyester nanofiber combined filament yarns obtained by combining 75T-112F (with a sea-island ratio of 30%:70% and an island number of 127/Filament) nanofibers and 22T-24F highly shrinkable yarns, a circularly knitted fabric was knitted. Next, the fabric was immersed in a 3% by mass aqueous sodium hydroxide solution (75° C., with a bath ratio of 1:30) to remove an easily soluble component, and a nanofiber-highly shrinkable yarn combined yarn-used knitted fabric was obtained. A polyurethane resin fine porous film was laminated on the back side of the obtained knitted fabric by a known method, whereas "Denatron FB408B" (manufactured by Nagase Chemtex Corporation) as an electric conductive resin-containing dispersion liquid was applied to the front side thereof to give an agent application amount of 15 g/m$^2$ by a known knife coating method to obtain an electric conductive fiber structure. Table 1 lists the used materials and the characteristics of the obtained electric conductive fiber structure.

Example 12

The same processing as that of Example 11 was performed except that the highly shrinkable yarns were changed from 22T-24F to 33T-6F to make polyester nanofiber combined filament yarns combined with 75T-112F (with a sea-to-island ratio of 30%:70% and an island number of 127/Filament) and that dyeing treatment was performed to manufacture an electric conductive fiber structure. Table 1 lists the used materials and the characteristics of the obtained electric conductive fiber structure.

Example 13

The same processing as that of Example 11 was performed except that the fabric structure was changed from the knitted fabric to a plain-woven fabric to manufacture an electric conductive fiber structure. Table 1 lists the used materials and the characteristics of the obtained electric conductive fiber structure.

Example 14

The same processing as that of Example 11 was performed except that the polyester nanofiber combined filament yarns were changed to 75T-112F (with a sea-island ratio of 30%:70% and an island number of 127/Filament) polyester nanofiber single yarns to manufacture an electric conductive fiber structure. Table 1 lists the used materials and the characteristics of the obtained electric conductive fiber structure.

Example 15

The same processing as that of Example 11 was performed except that the polyester nanofiber combined filament yarns were changed to 100T-30F (with a sea-island ratio of 30%:70% and an island number of 2,048/Filament) polyester nanofiber single yarns to manufacture an electric conductive fiber structure. Table 1 lists the used materials and the characteristics of the obtained electric conductive fiber structure.

Example 16

The same processing as that of Example 11 was performed except that the polyester nanofiber combined filament yarns were changed to 120T-60F (with a sea-island ratio of 50%:50% and an island number of 2,048/Filament) polyester nanofiber single yarns to manufacture an electric conductive fiber structure. Table 1 lists the used materials and the characteristics of the obtained electric conductive fiber structure.

Example 17

The same processing as that of Example 11 was performed except that the polyester nanofiber combined filament yarns were changed to 75T-112F (with a sea-island ratio of 30%:70% and an island number of 127/Filament) triangular-cross-section polyester nanofiber single yarns to manufacture an electric conductive fiber structure. Table 1 lists the used materials and the characteristics of the obtained electric conductive fiber structure.

Example 18

The same processing as that of Example 11 was performed except that the 22T-24F highly shrinkable yarns were not used and that 75T-112F (with a sea-island ratio of 30%:70% and an island number of 127/Filament) was changed to a circularly knitted fabric obtained using 66T-9F (with a sea-island ratio of 20%:80% and an island number of 70/Filament) microfibers to manufacture an electric conductive fiber structure. Table 1 lists the used materials and the characteristics of the obtained electric conductive fiber structure.

Example 19

A needle punched nonwoven fabric formed using polymer arrangement fibers (with a sea-island ratio of 57%:43% and an island number of 16) with 4.2 dtex, a length of 51 mm, polyethylene terephthalate as an island component, and polystyrene as a sea component was impregnated with polyurethane and was subjected to wet solidification. The content of polyurethane was 49% relative to the mass of polyethylene terephthalate. The nonwoven fabric was immersed in trichloroethylene and was squeezed with a mangle to remove a polystyrene component to obtain ultrafine fibers with a monofilament fineness of 0.15 dtex. With a buffing machine, a nonwoven fabric with fluffing processing and dyeing treatment performed was obtained. Similarly to Example 11, a polyurethane resin fine porous film was laminated on the back side of the obtained nonwoven fabric, whereas "Denatron FB408B" (manufactured by Nagase Chemtex Corporation) as an electric conductive resin-containing dispersion liquid was applied to the front side thereof to give an agent application amount of 20 g/m$^2$ by a known knife coating method to obtain an electric conductive fiber structure. Table 1 lists the used materials and the characteristics of the obtained electric conductive fiber structure.

Example 20

The same processing as that of Example 1 was performed except that the polyester nanofibers in Example 5 were changed to nylon nanofibers to manufacture an electric conductive fiber structure. Table 1 lists the used materials and the characteristics of the obtained electric conductive fiber structure.

Comparative Example 1

The same processing as that of Example 1 was performed except that the electric conductive resin-containing dispersion liquid was changed from "Denatron FB408B" to "Seplegyda OC-AE401," in which an acrylic resin is used as a binder, (manufactured by Shin-Etsu Polymer Co., Ltd.) to manufacture an electric conductive fiber structure. Table 1 lists the used materials and the characteristics of the obtained electric conductive fiber structure.

Comparative Example 2

"Denatron FB408B" (manufactured by Nagase Chemtex Corporation) as an electric conductive resin-containing dispersion liquid was applied to a PET film to give an agent application amount of 15 g/m$^2$ by a known knife coating method to obtain an electrode. Table 1 lists the used materials and the characteristics of the obtained film.

TABLE 1

|  | Filament | Polymer | Cross section | Fiber diameter | Used yarn | Variations in fiber diameter (CV % (A)) | Variations in modification degree (CV % (B)) |
|---|---|---|---|---|---|---|---|
| Example 1 | Multifilament/ highly shrinkable yarn | Polyester | Circle | 700 nm | 75T-112F (sea:island = 30%:70%)/22T-24F | 5 | 7 |
| Example 2 | Multifilament/ highly shrinkable yarn | Polyester | Circle | 700 nm | 75T-112F (sea:island = 30%:70%)/22T-24F | 5 | 7 |
| Example 3 | Multifilament/ highly shrinkable yarn | Polyester | Circle | 700 nm | 75T-112F (sea:island = 30%:70%)/33T-6F | 5 | 7 |
| Example 4 | Multifilament/ highly shrinkable yarn | Polyester | Circle | 700 nm | 75T-112F (sea:island = 30%:70%)/22T-24F | 5 | 7 |
| Example 5 | Multifilament | Polyester | Circle | 700 nm | 75T-112F (sea:island = 30%:70%) | 5 | 7 |
| Example 6 | Multifilament | Polyester | Circle | 300 nm | 100T-30F (sea:island = 30%:70%) | 3 | 3.4 |
| Example 7 | Multifilament | Polyester | Circle | 200 nm | 120T-60F (sea:island = 50%:50%) | 3 | 3.4 |

TABLE 1-continued

| | | | | | | | |
|---|---|---|---|---|---|---|---|
| Example 8 | Multifilament | Polyester | Triangle | 700 nm | 75T-112F (sea:island = 30%:70%) | 3 | 3.4 |
| Example 9 | Multifilament | Polyester | Circle | 2,700 nm | 66T-9F (sea:island = 20%:80%) | 6 | 9 |
| Example 10 | Multifilament | Polyester | Circle | 3,800 nm | Single yarn fineness 0.15 dtex | 6 | 9 |
| Example 11 | Multifilament/ highly shrinkable yarn | Polyester | Circle | 700 nm | 75T-112F (sea:island = 30%:70%)/22T-24F | 5 | 7 |
| Example 12 | Multifilament/ highly shrinkable yarn | Polyester | Circle | 700 nm | 75T-112F (sea:island = 30%:70%)/33T-6F | 5 | 7 |
| Example 13 | Multifilament/ highly shrinkable yarn | Polyester | Circle | 700 nm | 75T-112F (sea:island = 30%:70%)/22T-24F | 5 | 7 |
| Example 14 | Multifilament | Polyester | Circle | 700 nm | 75T-112F (sea:island = 30%:70%) | 5 | 7 |
| Example 15 | Multifilament | Polyester | Circle | 300 nm | 100T-30F (sea:island = 30%:70%) | 3 | 3.4 |
| Example 16 | Multifilament | Polyester | Circle | 200 nm | 120T-60F (sea:island = 50%:50%) | 3 | 3.4 |
| Example 17 | Multifilament | Polyester | Triangle | 700 nm | 75T-112F (sea:island = 30%:70%) | 3 | 3.4 |
| Example 18 | Multifilament | Polyester | Circle | 2,700 nm | 66T-9F (sea:island = 20%:80%) | 6 | 9 |
| Example 19 | Multifilament | Polyester | Circle | 3,800 nm | Single yarn fineness 0.15 dtex | 6 | 9 |
| Example 20 | Multifilament | Nylon | Circle | 700 nm | 75T-112F (sea:island = 30%:70%) | 5 | 7 |
| Comparative Example 1 | Multifilament/ highly shrinkable yarn | Polyester | Circle | 700 nm | 75T-112F (sea:island = 30%:70%)/22T-24F | 5 | 7 |
| Comparative Example 2 | R-PET film | — | — | — | — | — | — |

| | Density (number/in) Longitudinal × lateral | Weight per unit area (g/m$^2$) | Fiber structure | Name of agent | Electric Conductive Resin Impregnation area ratio (%) | Electric Conductive Resin Impregnation area ratio (%) (washing) | Electric Conductive resin dispersion particle diameter |
|---|---|---|---|---|---|---|---|
| Example 1 | 58 × 78 | 118 | Knitted fabric | Denatron FB408B | 20.7 | 12.2 | Less than 200 nm |
| Example 2 | 58 × 78 | 118 | Knitted fabric | Denatron TX401 | 18.3 | 11.5 | Less than 200 nm |
| Example 3 | 46 × 110 | 194 | Knitted fabric | Denatron FB408B | 23.2 | 13.3 | Less than 200 nm |
| Example 4 | 216 × 113 | 98 | Woven fabric | Denatron FB408B | 20.2 | 11.8 | Less than 200 nm |
| Example 5 | 43 × 58 | 112 | Knitted fabric | Denatron FB408B | 28.3 | 15.5 | Less than 200 nm |
| Example 6 | 58 × 78 | 110 | Knitted fabric | Denatron FB408B | 29.2 | 15.3 | Less than 200 nm |
| Example 7 | 70 × 94 | 98 | Knitted fabric | Denatron FB408B | 27.5 | 12.3 | Less than 200 nm |
| Example 8 | 43 × 58 | 115 | Knitted fabric | Denatron FB408B | 28.2 | 16.2 | Less than 200 nm |
| Example 9 | 114 × 118 | 61 | Woven fabric | Denatron FB408B | 15.7 | 10.3 | Less than 200 nm |
| Example 10 | — | 135 | Nonwoven fabric | Denatron FB408B | 16.4 | 12.2 | Less than 200 nm |
| Example 11 | 58 × 78 | 118 | Knitted fabric | Denatron FB408B | 21.5 | 13.2 | Less than 200 nm |
| Example 12 | 46 × 110 | 194 | Knitted fabric | Denatron FB408B | 19.3 | 11.8 | Less than 200 nm |
| Example 13 | 216 × 113 | 98 | Woven fabric | Denatron FB408B | 24.3 | 12.5 | Less than 200 nm |
| Example 14 | 43 × 58 | 112 | Knitted fabric | Denatron FB408B | 23.2 | 11.9 | Less than 200 nm |
| Example 15 | 58 × 78 | 110 | Knitted fabric | Denatron FB408B | 28.8 | −15.8 | Less than 200 nm |
| Example 16 | 70 × 94 | 98 | Knitted fabric | Denatron FB408B | 29.5 | 15.5 | Less than 200 nm |
| Example 17 | 43 × 58 | 115 | Knitted fabric | Denatron FB408B | 27.5 | 12.3 | Less than 200 nm |
| Example 18 | 114 × 118 | 61 | Knitted fabric | Denatron FB408B | 16.5 | 10.5 | Less than 200 nm |
| Example 19 | — | 135 | Nonwoven fabric | Denatron FB408B | 17.2 | 13.2 | Less than 200 nm |
| Example 20 | 45 × 60 | 115 | Knitted fabric | Denatron FB408B | 16.4 | 12.2 | Less than 200 nm |

TABLE 1-continued

| | | | | | | | | | | |
|---|---|---|---|---|---|---|---|---|---|---|
| Comparative Example 1 | 58 × 78 | 118 | Knitted fabric | Seplegyda OC-AE401 | | | 10.9 | 0 | 200 nm or more | |
| Comparative Example 2 | — | 140 | Film | Denatron FB408B | | | Unmeasurable | Unmeasurable | Less than 200 nm | |

| | Conductive Resin Average Particle diameter | Resin Adhesion Amount (g/m$^2$) | Water-Proof And Moisture penetration | Dyeing | Chemical treatment | Physical treatment | Resistance (Ω) | Resistance (washing) | Bending resistance (mm) Longitudinal × lateral | Peeling | Anti-Bacterial activity |
|---|---|---|---|---|---|---|---|---|---|---|---|
| Example 1 | 14 nm | 12.3 | — | — | — | — | 10.3 | 7.5 × 10$^2$ | 53 × 68 | A | 4.9 |
| Example 2 | 19 nm | 15.3 | — | — | — | — | 12.5 | 2.5 × 10$^3$ | 51 × 63 | A | 3.5 |
| Example 3 | 15 nm | 13.5 | — | ○ | — | — | 9.8 | 6.2 × 10$^2$ | 64 × 72 | A | 5.0 |
| Example 4 | 16 nm | 9.8 | — | — | — | — | 11.3 | 2.3 × 10$^3$ | 47 × 40 | A | 4.8 |
| Example 5 | 14 nm | 12.2 | — | — | — | — | 10.3 | 4.5 × 10$^2$ | 12 × 12 | A | 5.2 |
| Example 6 | 14 nm | 12.3 | — | — | — | — | 10.2 | 3.2 × 10$^2$ | 10 × 11 | A | 5.3 |
| Example 7 | 14 nm | 9.7 | — | — | — | — | 11.4 | 5.8 × 10$^2$ | 10 × 11 | A | 4.6 |
| Example 8 | 14 nm | 12.5 | — | — | — | — | 10.4 | 2.4 × 10$^2$ | 13 × 15 | A | 4.9 |
| Example 9 | 17 nm | 8.9 | — | — | — | — | 10.9 | 8.9 × 10$^2$ | 39 × 27 | A | 4.8 |
| Example 10 | 15 nm | 12.8 | — | ○ | PU | Napping | 10.5 | 4.1 × 10$^3$ | 42 × 43 | A | 4.9 |
| Example 11 | 14 nm | 14.5 | PU fine porous | — | — | — | 9.5 | 6.3 × 10$^2$ | 52 × 58 | A | 5.3 |
| Example 12 | 17 nm | 15.3 | PU fine porous | ○ | — | — | 8.9 | 5.4 × 10$^2$ | 58 × 60 | A | 5.5 |
| Example 13 | 14 nm | 10.9 | PU fine porous | — | — | — | 10.8 | 7.5 × 10$^2$ | 69 × 59 | A | 4.8 |
| Example 14 | 14 nm | 14.2 | PU fine porous | — | — | — | 9.7 | 6.6 × 10$^2$ | 28 × 33 | A | 5.1 |
| Example 15 | 16 nm | 14.1 | PU fine porous | — | — | — | 9.7 | 2.3 × 10$^2$ | 29 × 30 | A | 5.1 |
| Example 16 | 14 nm | 12.6 | PU fine porous | — | — | — | 10.4 | 4.5 × 10$^2$ | 25 × 27 | A | 4.8 |
| Example 17 | 17 nm | 14.3 | PU fine porous | — | — | — | 9.4 | 4.3 × 10$^2$ | 31 × 32 | A | 5.1 |
| Example 18 | 14 nm | 8.2 | PU fine porous | — | — | — | 11.8 | 0.9 × 10$^4$ | 76 × 78 | A | 4.3 |
| Example 19 | 15 nm | 12.8 | PU fine porous | ○ | PU | Napping | 10.2 | 2.6 × 10$^3$ | 42 × 43 | A | 4.8 |
| Example 20 | 16 nm | 13.5 | — | — | — | — | 9.9 | 7.9 × 10$^2$ | 25 × 33 | A | 5.0 |
| Comparative Example 1 | 55 nm | 12.3 | — | — | — | — | 35.8 | 10$^6$ or more | 50 × 62 | B | 2.0 |
| Comparative Example 2 | 14 nm | 14.9 | — | — | — | — | 12.4 | 10$^6$ or more | 95 | B | 3.0 |

The invention claimed is:

1. An electric conductive fiber structure comprising:
a fiber structure including single fibers; and
an electric conductive resin containing electric conductive polymer(s), the electric conductive resin being supported in a surface of the single fibers and being filled in gaps between the single fibers, the electric conductive fiber structure having 15% or more area ratio of the electric conductive resin present in an area of 15 to 30 µm from a surface of the electric conductive fiber structure when a cross section in a thickness direction of the electric conductive fiber structure is observed, the electric conductive resin having a dispersion particle diameter of less than 200 nm and having an average particle diameter of 20 nm or less.

2. The electric conductive fiber structure according to claim 1, wherein the electric conductive resin further contains binder resin(s).

3. The electric conductive fiber structure according to claim 2, wherein the binder resin is olefinic resin(s).

4. The electric conductive fiber structure according to claim 1, wherein main components of the electric conductive polymer are poly(3,4-ethylenedioxythiophene) and polystyrene sulfonic acid.

5. The electric conductive fiber structure according to claim 1 having antibacterial activity.

6. The electric conductive fiber structure according to claim 1 having an antibacterial activity value of 3 or more by JIS L 1902 (2015 Edition).

7. The electric conductive fiber structure according to claim 1 having single fiber(s) of which diameter(s) is/are 10 nm or more and 5,000 nm or less in a part or all.

8. The electric conductive fiber structure according to claim 1 having a surface resistance of 1×10$^4$Ω or less after repeating washing 30 times by JIS L 0217 (1995 Edition) 103 method.

9. An electrode member comprising the electric conductive fiber structure according to claim 1 for use in acquisition of a biosignal.

10. A method of producing an electric conductive fiber structure comprising a fiber structure including single fibers; and an electric conductive resin containing electric conductive polymer(s), the electric conductive resin being supported in a surface of the single fibers and filled in gaps between the single fibers, the electric conductive fiber structure having 15% or more area ratio of the electric conductive resin present in an area of 15 to 30 µm from a surface of the electric conductive fiber structure when a cross section in a thickness direction of the electric conductive fiber structure is observed, the electric conductive resin having a dispersion particle diameter of less than 200 nm and having an average particle diameter of 20 nm or less, the method comprising a process that an electric conductive resin containing an electric conductive polymer, having a dispersion particle diameter of less than 200 nm, and having an average particle diameter of 20 nm or less is supported in the surface of the single fibers included in a fiber structure and is filled in the gaps between the single fibers included in a fiber structure.

11. The method according to claim 10, wherein the electric conductive resin contains a mixture of the electric conductive polymer(s) and binder resin(s) as a main component.

* * * * *